(12) United States Patent
Ebeler et al.

(10) Patent No.: US 9,188,568 B2
(45) Date of Patent: Nov. 17, 2015

(54) GAS CHROMATOGRAPHY RECOMPOSITION-OLFACTOMETRY FOR CHARACTERIZATION OF AROMA MIXTURES

(71) Applicant: THE REGENTS OF THE UNIVERSITY OF CALIFORNIA, Oakland, CA (US)

(72) Inventors: Susan E. Ebeler, Davis, CA (US); Arielle Johnson, Davis, CA (US); Greg Hirson, Charlottesville, VA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 429 days.

(21) Appl. No.: 13/767,798

(22) Filed: Feb. 14, 2013

(65) Prior Publication Data
US 2013/0219991 A1 Aug. 29, 2013

Related U.S. Application Data

(60) Provisional application No. 61/598,712, filed on Feb. 14, 2012.

(51) Int. Cl.
*G01N 30/02* (2006.01)
*G01N 30/72* (2006.01)
(Continued)

(52) U.S. Cl.
CPC ............ *G01N 30/02* (2013.01); *G01N 30/7206* (2013.01); *G01N 30/78* (2013.01); *G01N 30/84* (2013.01); *G01N 2030/8411* (2013.01); *G01N 2030/8809* (2013.01)

(58) Field of Classification Search
CPC ...................................................... G01N 30/02
USPC ............. 73/23.34, 23.35, 23.37, 23.39–23.41
See application file for complete search history.

(56) References Cited

U.S. PATENT DOCUMENTS 7,666,685 B2 * 2/2010 Bazemore et al. ............ 436/120
2002/0182739 A1 * 12/2002 Sadik et al. .................... 436/106
(Continued)

OTHER PUBLICATIONS

Sasamoto et al., Selectable one-dimensional or two-dimensional gas chromatography-mass spectrometry with simultaneous oltl ctometry or eRment-specific detection.; Journal of Chromatography A, 2010, pp. 2903-2910.*

(Continued)

*Primary Examiner* — Hezron E Williams
*Assistant Examiner* — Hoang Nguyen
(74) *Attorney, Agent, or Firm* — John P. O'Banion

(57) ABSTRACT

A method for the in-instrument recombination of volatiles using a gas chromatograph with mass spectrometry and olfactometry detection is described. Compounds that are introduced into the modified GC are separated conventionally on an analytical capillary GC column. The elution profile of volatiles can be segmented, analyzed and arbitrarily combined. In-line with the GC column, a pneumatic flow switch and splitter are connected to a detector and olfactometer. A cold trap allows the user to build a mixture of separated volatiles that is held until the cryotrap is rapidly heated, releasing the mixture for a subject to smell at the olfactory port and to evaluate. The instrument allows for characterization of the aroma quality of specific fractions of aroma volatiles obtained from foods, flowers or beverages without the need for pure chemical standards or the calculation of individual compound concentrations or sensory thresholds.

20 Claims, 6 Drawing Sheets

(51) Int. Cl.
 G01N 30/78 (2006.01)
 G01N 30/84 (2006.01)
 G01N 30/88 (2006.01)

(56) References Cited

U.S. PATENT DOCUMENTS

2005/0252275 A1* 11/2005 Kita et al. ............... 73/23.34
2013/0143247 A1* 6/2013 Haick et al. ............. 435/15

OTHER PUBLICATIONS

W. Grosch, Evaluation of the Key Odorants of Foods by DiBution Experiments, Aroma Models and Omission; Chem. Senses 26: 533-545, 2001.*

Perez-Silva et al., GC-MS and GC-olfactometry analysis of aroma compounds in a representative organic aroma extract from cured vanilla (Vanilla planifolia G. Jackson) beans; Science Direct, food Chemistry 99 (2006), pp. 728-735.*

Plutowska et al., Application of gas chromatography-olfactometry (GC-O) in analysis and quality assessment of alcoholic beverages—A review; Science Direct, Food Chemistry 107 (2008), pp. 449-463.*

Ryan et al., The sinificant of low impact odorants in global odour perception; Trends in Food Science & Technology 19 (2008) 383-389.*

Abbott, N. et al. "Evaluation of the Representativeness of the Odor of Beer Extracts Prior to Analysis by GC Eluate Sniffing," J. Agric. Food Chem., 1993, vol. 41, pp. 777-780.

Acree, T.E., "A Procedure for the Sensory Analysis of Gas Chromatographic Effluents," Food Chemistry, vol. 14, 1984, pp. 273-286.

Axel, R., "Scents and Sensibility: A Molecular Logic of Olfactory Perception," Nobel Lecture, Dec. 8, 2004, Howard Hughes Medical Institute, Columbia University, College of Physicians and Surgeons, pp. 234-256.

Buck, L., "Unraveling the Sense of Smell," Nobel Lecture, Dec. 8, 2004, Howard Hughes Medical Institute, Fred Hutchinson Cancer Research Center, pp. 267-283.

Bult, J. et al "The Influence of Olfactory Concept in the Probability of Detecting Sub- and Pen-threshold Components in a Mixture of Odorants," Chem. Senses, 2001, vol. 26, pp. 459-469.

Escudero, A., et al., "Characterization of the Aroma of a Wine from Maccabeo. Key Role Played by Compounds with Low Odor Activity Values," J. Agric. Food Chem. 2004, vol. 52, pp. 3516-3524.

Grosch, W., "Detection of Potent odorants in foods by aroma extract dilution analysis," Trends in Food Science & Technology, vol. 4, Mar. 1993, pp. 68-73.

Grosch, W., "Evaluation of the Key Odorants if Foods by Dilution Experiments, Aroma Models and Omission," Chem. Senses, 2001, vol. 26, pp. 533-545.

Laing, D.G., et al. "Quality and Intensity of Binary Odor Mixtures," Physiology & Behavior, 1983, vol. 33, pp. 309-319.

Laing, D.G., et al. "The limited capacity of humans to identify the components of taste mixtures and taste—odour mixtures," Perception, 2002, vol. 31, pp. 617-635.

Laing, D.G., et al. "Relationship between Molecular Structure, Concentration and Odor Qualities of Oxygenated Aliphatic Molecules," Chem. Senses, 2003, vol. 28, pp. 57-69.

Le Berre, E., et al., "Just Noticeable Differences in Component Concentrations Modify the Odor Quality of a Blending Mixture," Chem. Senses, Feb. 27, 2008, vol. 33, pp. 389-395.

Le Berre, E., et al., "Perceptual Processing Strategy and Exposure Influence the Perception of Odor Mixtures," Chem. Senses, Dec. 10, 2007 vol. 33, pp. 193-199.

Ochiai, N. and Sasamoto, K., "Selectable one-dimensional or two-dimensional gas chromatography—olfactometry/mass spectrometry with preparative fraction collection for analysis of ultra-trace amounts of odor compounds," Journal of Chromatography A, Oct. 11, 2010, pp. 3180-3185.

Patton and Josephson, "A method for determining significance of volatile flavor compounds in foods," Pennsylvania Agricultural Experiment Station, Jan. 10, 1957, pp. 316-318.

Perez-Silva, et al., "GC-MS and GC-olfactometry analysis of aroma compounds in a representative organic aroma extract from cured vanilla (Vanilla planifolia G. Jackson) beans," Food Chemistry, 2006, vol. 99, pp. 728-735.

Pineau., et al., "Which Impact for â-Damascenone on Red Wines Aroma?" J. Agric. Food Chem. 2007, 55, pp. 4103-4108.

Plutowska and Wardencki, "Application of gas chromatography-olfactometry (GC-O) in analysis and quality assessment of alcoholic beverages—A review," Food Chemistry, 2008, vol. 107, pp. 449-463.

Poinot, P., et al., "Optimisation of HS-SPME to study representativeness of partially baked bread odorant extracts," Food Research International, 2007, vol. 40, pp. 1170-1184.

Ryan, D., "The significance of low impact odorants in global odour perception," Trends in Food Science & Technology 19, 2008, pp. 383-389.

San-Juan, F., "Producing headspace extracts for the gas chromatography-olfactometric evaluation of wine aroma," Food Chemistry, 2010, vol. 123, pp. 188-195.

Sasamoto and Ochiai, "Selectable one-dimentional or two-dimentional gas chromatography-mass spectrometry with simultaneous olfactory or element-specific detection," Journal of Chromatography A, Feb. 25, 2010, pp. 2903-2910.

Shepherd, G.M., "Smell images and the flavour system in the human brain," Nature, Nov. 16, 2006, vol. 444. pp. 316-321.

* cited by examiner

GAS CHROMATOGRAPHY RECOMPOSITION-OLFACTOMETRY FOR CHARACTERIZATION OF AROMA MIXTURES

CROSS-REFERENCE TO RELATED APPLICATIONS

This application claims priority from U.S. provisional patent application Ser. No. 61/598,712 filed on Feb. 14, 2012, incorporated herein by reference in its entirety.

STATEMENT REGARDING FEDERALLY SPONSORED RESEARCH OR DEVELOPMENT

This invention was made with Government support under Grant Number 1148897 awarded by the National Science Foundation (NSF). The Government has certain rights in the invention.

INCORPORATION-BY-REFERENCE OF MATERIAL SUBMITTED ON A COMPACT DISC

Not Applicable

BACKGROUND OF THE INVENTION

1. Field of Invention

This invention pertains generally to the characterization and analysis of aromatic mixtures, and more particularly to human perceptual characterization and analysis of aromatic mixtures using in-instrument gas chromatography recomposition-olfactometry methods and apparatus.

2. Background

Aromas are typically mixtures of small volatile molecules that are able to stimulate a physiological response in low concentrations. Volatile chemicals that are present in inhaled air stimulate olfactory receptors and nerves in the nasal epithelium producing a signal that is transmitted to the brain. Processing of the signal by the brain includes a comparison with previously experienced smells, accounting for the high subjectivity seen in human aroma perceptions. Aromas also play a dominant role in the multisensory perception of flavor.

The mammalian olfactory system is a highly complex and efficient odor detection system derived from millions of years of evolutionary development. More than a thousand olfactory genes have been identified that produce receptor proteins involved in the interpretation of aromas and account for about two percent of the known genes in the genome.

Large numbers of olfactory receptors provide a system that is capable of detecting and discriminating between many different aroma compounds because the receptors have a broad sensitivity and may be activated by different aroma molecules with similar molecular structures. In addition, the majority of aroma molecules are capable of activating more than one type of olfactory receptor. Consequently, different combinations of receptors may be activated by a particular aroma molecule. The possible combinations of activated receptors are substantial so that the overall olfactory system is able to detect thousands of different molecules, even those that have not been encountered before.

The experienced perception of the group of aroma compounds that is sensed from the environment is considered to be the smell or aroma of a particular material. The aroma-derived components of flavors are perceptual constructs created by the brain in response to stimulation of the olfactory system as the brain detects and interprets mixtures of volatile chemicals and mixtures.

Quantifying the relationship between aroma perception and chemical composition in complex mixtures such as foods and beverages has been complicated by the observed complexity of aroma mixtures, the subjective olfactory memory and description standardizations. Generally, the chemical analysis of mixtures of odorous compounds can be complicated due to the phenomena of synergy, inhibition and masking that can take place between different compounds. Furthermore, when mixtures of aroma molecules combine, some of the aroma components in the resulting mixture may delete or accentuate the contributions of other aroma molecules creating unexpected perceptual results.

Approaches that are based on analytical chemistry for characterizing aromas or flavors typically rely on separation-based chromatographic methods that quantify the aroma strength of individual compounds in a mixture, reflected as either the concentration present in the mixture divided by a measured sensory threshold concentration (Odor Activity Value, OAV) or the number of N-fold dilutions required to suppress detectability of a compound when analyzed by gas chromatography with a human subject acting as an olfactory detector (GC-Olfactometry or GC-O; CHARM; or Aroma Extract Dilution Analysis). Reconstitution and omission experiments evaluate the role of specific compounds in the perceived aroma of a mixture, whereby a blend of compounds hypothesized to be detectable in a food, beverage, or other sample by OAV is mixed from chemical standards, and compared to similar mixtures prepared by omitting one of these compounds at a time. If a difference is detectable in the "whole" mix versus a "whole-minus-one-compound" mix, that particular compound is considered important to the aroma of the sample.

Knowledge acquired from other disciplines studying aromas, such as sensory psychophysics, cognitive psychology, and molecular neurobiology, suggest that there are limitations in these methodologies. Chromatographic techniques only assess the aroma quality of individual compounds, rather than mixtures of compounds. However, the aroma of a mixture is frequently perceptually distinct from that of its individual components and may have qualities not found in any of these individual components. The mixing-dependent nature of aroma quality is evidenced by the relative lack of aroma impact compounds, or those compounds that are singularly responsible for the overall aroma impression of a food or beverage. On the other hand, omission experiments rely on an assumption that all sensorially important compounds have been correctly identified and quantified and that any compound occurring at a concentration below its putative sensory threshold is not important to the overall aroma. However, this assumption is not always accurate. Despite having identical concentration profiles of supra-threshold odorants, the aroma of a reconstitution sometimes still smells different from the original mixture, a phenomenon referred to as "reconstitution discrepancy".

Accordingly, there is a need for an apparatus and method of identifying and quantifying subsets of aroma compounds and the contribution of the compounds on the perceived aroma. There is also a need for an apparatus and method that is accurate and can reliably show the relation between the aroma mixture composition and olfactory perception regardless of concentration so that models can be created. The present invention satisfies these needs as well as others and is generally an improvement over the art.

SUMMARY OF THE INVENTION

The perception of aroma and flavor has often been approached as a problem of many individual parts, with chemistry, neurobiology, sensory science, psychology, and other disciplines focused on answering questions about some aspect of the relationship between stimulus (a flower, a glass of wine, a plate of food), response (perceived flavor, liking or disliking, intake and satiety), or the pathway between the two (genetics, receptor binding, transduction, translation to cortical neurons). This has yielded a great deal of information about those individual parts, but not a well-developed understanding of how they work together for complex, everyday stimuli and activities like eating and drinking.

The present invention generally provides a novel platform and methods for assessing the perceptual effect of mixing an arbitrary number of volatile compounds from a mixture without the need for reconstitution with pure chemical standards. The design allows for the in-instrument gas chromatographic preparation of mixtures containing precise sections from a sample's chromatogram, up to and including the entire volatile fraction, allowing for aroma characterization of the impact of one or a few volatiles in a complex mixture.

Generally, the apparatus permits a series of non-reductive, in-instrument recombination and omission experiments using a Gas Chromatograph modified with a flow switch and then a cold trap in-line between the capillary column and the chemical and olfactory detectors to characterize aromas.

In the preferred embodiment of the apparatus for characterization and analysis of aroma mixtures, an instrument such as a gas chromatograph-mass spectrometer detector (GC-MSD) that has a separation column with an inlet and an outlet is used. The material from the column flows through a flow switch such as a Dean's switch directing flow to waste or to detection. The flow switch is coupled to a flow splitter that divides the flow of material between a mass spectrometer detector and a cryogenic trap and olfactory port for olfactory detection. A heater associated with the cryogenic trap is configured to release the trapped materials upon heating.

In use, volatiles may be extracted onto a solid phase (via solid-phase microextraction or SPME) from the headspace of a food, beverage, or other sample and initially they are separated conventionally on an analytical capillary GC column. In-line with the GC column is the pneumatic Deans Switch followed by a cold trap that allows the experimenter to build a mixture of these separated volatiles that is held until the cryotrap is rapidly heated, releasing the mixture for a subject to smell at the olfactory port for evaluation. The same mixture eluted from the column that is collected in the cold trap is analyzed by the detector so that the composition of the olfactory evaluation is identified.

The elution profile from the column can be segmented so that fractions of the eluent can be collected in one or more cryotraps for olfactory characterization. Multiple runs can also produce fractions that can be combined, even fractions of the same segment of the elution profile. Fractions and combined fractions can be individually characterized as well as mixed with the whole set of volatiles and evaluated.

According to one aspect of the invention an apparatus is provided for the segmentation of chromatographic eluents over time and the olfactory detection and chemical characterization of same segmented samples.

Another aspect of the invention is to provide a novel in-instrument recombination method for gas chromatography-olfactometry analysis of the aroma of mixtures. The method allows for the non-reductive characterization of complex aromas and flavors.

A further aspect of the invention is to provide a method that can be used to identify subsets of compounds in a sample that are responsible for the aroma character of the sample. The method does not require chemical standards, reductive aroma models, or the calculation of Odor Activity Values to identify important subsets of compounds that contribute to an aroma and flavor of a substance.

Another aspect of the invention is to provide a method that allows for the analysis of previously uncharacterized emergent perceptual properties of complex mixture interaction effects in everyday smell and flavor situations.

Yet another aspect of the invention is to provide an apparatus and method for evaluating the phenomena of synergy, addition, inhibition and masking between different aroma compounds in a variety of aroma mixtures.

Another aspect of the invention is to provide a system that can characterize subsets of molecules and their aroma activity, identify patterns and to form predictive models.

Further aspects of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Referring more specifically to the drawings, for illustrative purposes several embodiments of the apparatus and methods for gas chromatograph recomposition olfactometry of the present invention are depicted generally in FIG. 1 through FIG. 6. It will be appreciated that the methods may vary as to the specific steps and sequence and the apparatus may vary as to composition and structural details, without departing from the basic concepts as disclosed herein. The method steps are merely exemplary of the order that these steps may occur. The steps may occur in any order that is desired, such that it still performs the goals of the claimed invention.

Figure 1:
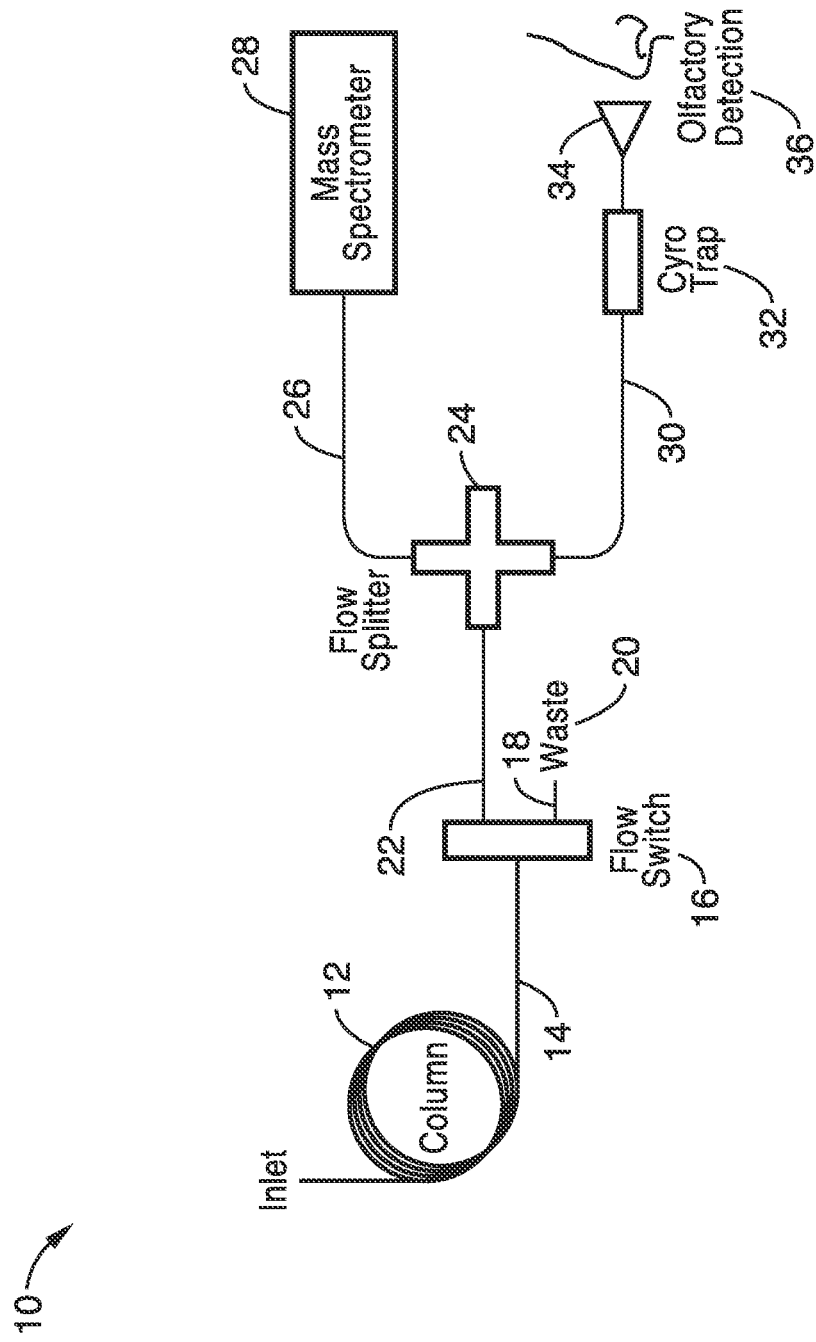
FIG. 1 is a schematic of an embodiment of an apparatus according to the invention.

Turning now to FIG. 1, a conceptual schematic of a gas chromatograph recomposition-olfactometer (GC-R) instrument 10 is shown. This design allows for the in-instrument gas chromatographic preparation of mixtures containing precise sections from a sample's chromatogram, up to and including the entire volatile fraction, permitting the aroma characterization of the impact of one or a few volatiles in a complex aroma mixture.

In the embodiment illustrated schematically in FIG. 1, volatile mixtures from samples of interest are obtained using standard analytical protocols (e.g., solvent extraction, distillation, filtration, etc.) and introduced to a gas chromatograph column 12 through an inlet. Column 12 that is used for separation is preferably an analytical capillary GC column. Although an analytical GC column is preferred, it will be understood that packed or other GC columns may also be used.

The separated volatiles from the sample are eluted from the column 12 over time through GC column outlet 14. Column outlet 14 is coupled to the inlet of a flow switch 16, preferably a Dean's switch. The flow switch 16 shown in FIG. 1 has an auxiliary pressure control and two flow switch outlets. The first flow switch outlet line 18 is connected to a waste container 20. The second flow switch outlet line 22 is connected to the intake of a flow splitter 24. Flow switch 16 controls the flow of the separated materials from the column 12 and directs it to flow splitter 24 or to waste 20.

The flow splitter 24 preferably divides and directs the flow through two outputs. The first splitter output 26 is coupled with at least one chemical detector 28. Detectors can be generally grouped as mass flow detectors and concentration dependent detectors and can provide different types of selectivity. Specific detectors respond to single chemical species while selective detectors respond to a range of compounds that have common chemical properties. Non-selective detectors respond to all compounds besides the carrier gas. In the embodiment of FIG. 1, the detector 28 is a mass spectrometer. However, any other gas chromatograph detectors 28 can also be used. For example, Flame Ionization (FID) and Photoionization (PID) detection can also be used in conjunction with or in place of the mass spectrometer detector 28.

The second splitter output line 30 connects the flow splitter 24 to a cryogenic trap 32. A heater that is connected to a control box and configured to switch the heater between an on state and an off state is preferably part of the cryogenic trap 32. The cryogenic trap 32 has an outlet that is attached to an olfactometry port 34 to permit olfactory detection 36.

In use, aroma mixtures are introduced into the inlet of a modified gas chromatograph and separated on the analytical column 12 in the usual manner. However, at the end of the column 12, the flow of carrier gas and analytes encounter a flow switch 16, such as a commercially available Deans switch, that can be set to direct the flow either towards the splitter 24 through switch outlet line 22 or towards the waste 20 to be contained or vented to an oven. The splitter 24 subsequently splits the flow of material from switch 16 to both a chemical detector 28 and to an olfactory port 34 for characterization. Along the transfer line 30 to the olfactory port 34 is a cryogenic trap 32, preferably controlled by a switch at the control box that allows the trap 32 to be cooled with liquid carbon dioxide (or liquid nitrogen) or heated so that the eluent is either held within the trap (i.e., cryotrapped) or released to the olfactory port 36. The pneumatic flow switch 16 followed by a cold trap 32 allows the user to build a mixture of these separated volatiles from the GC column 12 to be held until the cryotrap 32 is rapidly heated, releasing the mixture for a subject to smell at the olfactory port 34 and evaluation 36.

The flow splitter 24 that divides the flow from the GC column 12 permits the simultaneous chemical analysis from the mass spectrometer 28 and olfactory detection 36 of the same flow of compounds at the same time if necessary. Normally, the whole segment of the column output is kept in the cryogenic trap 32 and released to the olfactory port 34 by heating and thereafter evaluated with olfactometry.

Control over the flow switch 16 and splitter 24 permits a chemical evaluation over the whole set of separated aroma components as well as very narrow subsets of individual molecules or small groups of compounds that are delivered from the separation column 12 for analysis. The flow switch 16 also lets one or more sections of the chromatograph to be collected and combined in the cryogenic trap 32 using a chromatograph of the whole as a map.

Comparisons of the chemical detection and olfactometry results permit an evaluation of detected structures and perceived aromas to identify patterns and correlations as well as model development.

Figure 2:
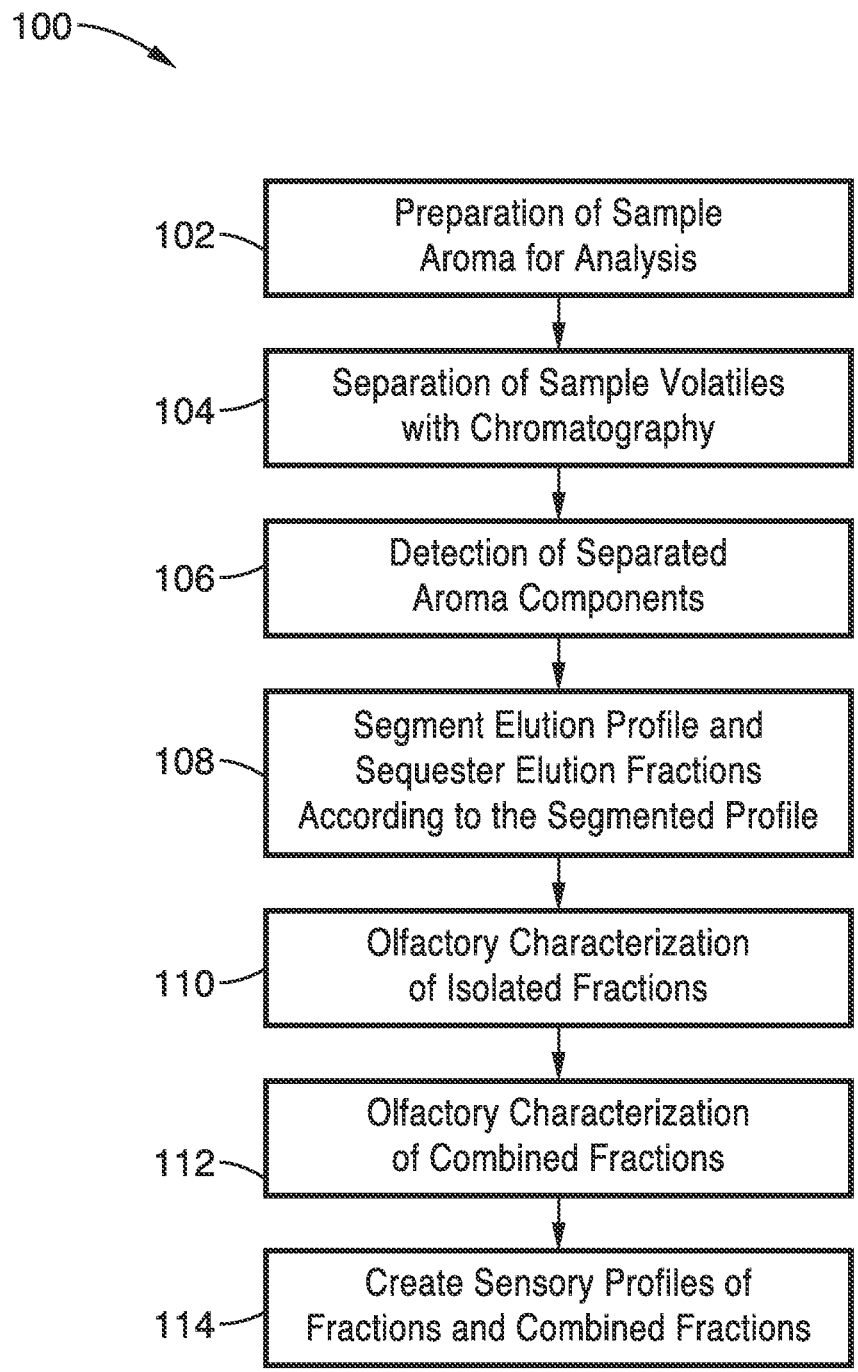
FIG. 2 is a flow diagram of a method for gas chromatography recomposition olfactometry according to one embodiment of the invention.
Figure 3:
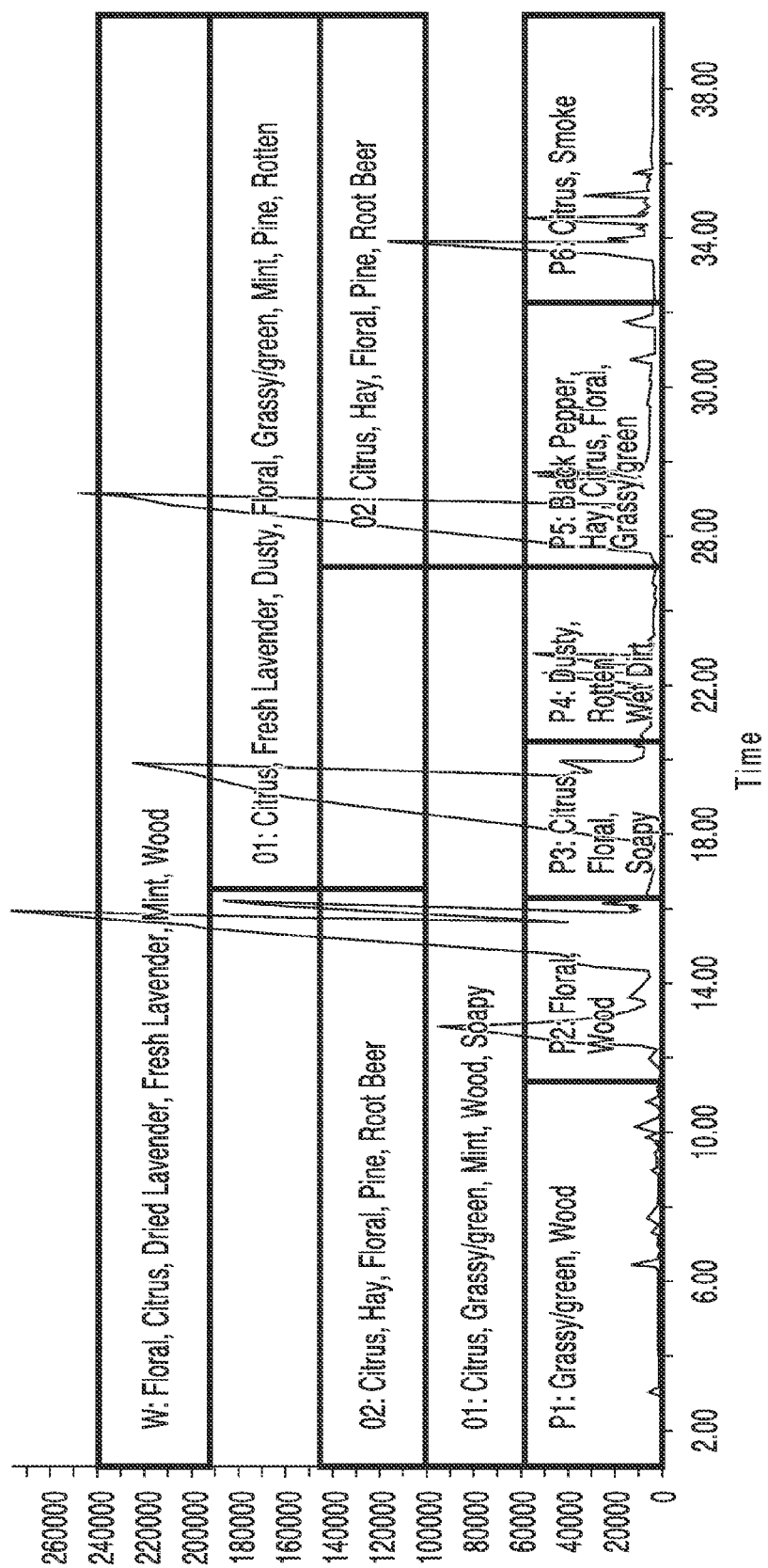
FIG. 3 is an example of a lavender chromatogram obtained with the invention overlaid with aroma descriptors for sections of the chromatogram of Table 1 showing cut times with selected fractions of lavender volatiles cryotrapped, eluted and smelled as mixtures.

Referring now to FIG. 2, one embodiment of the gas chromatography recomposition olfactometry method 100 is presented. Gas chromatography is a method for separating compounds that are capable of being vaporized without decomposing. At block 102, the sample aroma is prepared for analysis. Volatile compounds can be extracted from a sample in several conventional ways such as solvent extraction, distillation, filtration, etc. The preferred sample preparation of extracted volatiles at block 102 is with solid-phase microextraction (SPME) from the headspace of a food, beverage, or other sample. SPME has proven to be useful in extracting volatile components from the headspace of vessels containing aromas for subsequent analysis.

The sample that was prepared at block 102 is separated into component parts by gas chromatography at block 104. Gas chromatography is the preferred method of separation at block 104; however other separation methods can also be used. Gas chromatography is a process that separates components of a mixture primarily based on differences in boiling point or vapor pressure. The concentration of a particular compound in the gas phase is a function of the vapor pressure of the gas in this system.

The aroma components separated by the GC column may be detected at block 106. Chromatographic data is typically presented as a chromatogram composed of a spectrum of peaks for components eluting from the GC column at different times. The peaks represent column retention time (x-axis) as a function of detection (y-axis). The area under each peak can be calculated and the area is proportional to the quantity of component in the mixture so that the concentration of the component can be determined.

Detection and identification of individual components may be particularly important with the evaluation of samples with unknown elements. In one embodiment, a chromatogram for the full aroma is obtained and used as a baseline for segmenting the components for further analysis in other procedures. In another embodiment, the components are also analyzed and identified. However, quantitative analysis of the whole aroma and the identification of the individual components are optional.

At block 108, the elution profile from the column can be segmented based on time or by peak or groups of peaks. The elution from the column can be separated according to the segmented profile at block 108 and the fractions evaluated separately with olfactometry and mass spectrometry or other detector. The elution profile can also be used as a map to guide the selection of starting and ending points on the elution profile of each segment. Segments of the elution profile from the column can be of equal size e.g. covering the same amount of time of elution from the column. Segments at block 108 can also be selected based on peaks or groups of peaks rather than time. In this embodiment, segments of the elution profile will be of different sizes. The size of the peaks that are selected for the formation of segments may also be considered in the selection of segments. However, olfactory threshold information or component concentrations need not be known or considered in the selection of segment boundaries at block 108.

The segmented fractions of the elution profile that are selected and sequestered at block 108 can be evaluated through olfactometry and mass spectrometry in the embodiment of FIG. 2. The apparatus shown in FIG. 1 will permit the division of a single flow of material from the GC column and the simultaneous or sequential detection by mass spectrometry and olfactometry of the same material. In another embodiment, a chromatogram of the whole aroma is obtained and the olfactometry is conducted separately.

At block 110, the sequestered fractions are evaluated by olfactometry. In one embodiment, all of the sequestered fractions are evaluated by a panel of human assessors. The assessors formulate word classifiers of the odors of each fraction as part of the olfactometry. The olfactory descriptions and classifications of the smells of the isolated fractions provide an initial view of the contributions of the components or groups of components to the overall aroma under evaluation. These classifications can also assist in the selection of the fractions that are to be combined at block 112.

The olfactory characterization of the sequestered fractions of the segmented elution profile is preferably based on the fraction as a whole rather than with identified components in the fraction. The fractions can also be evaluated separately or as part of a combination of fractions regardless of the position of the fraction in the elution profile.

At block 112, selected sequestered fractions may be recombined and the combination evaluated by olfactometry. It is possible to build mixtures of subsets of volatiles in-instrument that can be characterized their aroma qualities with a sensory panel of assessors. A wide variety of combinations of segments from one or more runs can be collected, characterized and compared with the whole aroma.

Accordingly, selected compounds that elute off of the GC column can be collected as they elute off of the column and combined into a mixture for sensory analysis. Using the chromatogram of a mixture as a map, the GC-R instrument allows the operator to segment and recombine the components of the mixture at will, selecting compounds, peaks, or sections based on retention time to include or exclude in a reconstitution for sensory analysis. Selective recombination is accomplished with the flow switch that is directly in-line with the column, which directs compounds either to waste or to a cryotrap at the operator's discretion.

This system and method enables the creation of aroma reconstitutions incorporating all of the volatiles in segments of the sample, including instrumentally undetectable compounds as well those present at concentrations below sensory thresholds, thus correcting for the "reconstitution discrepancy" sometimes noted in flavor chemistry studies. This can be accomplished without the need for chemical standards, reductive aroma models, or calculation of Odor Activity Values, and is broadly applicable to any aroma or flavor.

The olfactory characterization of the fractions at block 110 and the combined fractions at block 112 using descriptive classifiers by human assessors can be further analyzed statistically, for example with correspondence analysis, to evaluate the sensory similarity of the segment fractions or combinations of fractions. The effects of the combinations of the segmented fractions at block 112 can also be evaluated and compared with the whole aroma. Synergistic effects, masking, additive effects and other trends can be elucidated. In addition, the compounds that have been optionally identified in the fractions of the segmented elution profile can also be compared with the olfactory descriptors to assign importance to the various compounds relative to the whole aroma.

At block 114, a sensory profile of the fractions and combined fractions can be optionally created with the mass spectrometry data, olfactometry data and comparison data. The profiles of fractions, mixtures of fractions and the whole chromatogram can be compared with the sensory profiles of other aromas and aroma components from other sources.

The embodiment of the method illustrated in FIG. 2 is particularly suited for analysis of samples with volatiles that are unknown or many components with complex interactions. In such cases it may be desirable to quantify and characterize each segmented portion of the elution profile. However, in other cases it may be desirable to reduce the number of olfactory characterizations at block 110 and 112 as well as reduce the number of compounds that are identified by mass spectroscopy or other detectors that are used.

In another embodiment, the sample is prepared and volatiles extracted for analysis at block 102 followed by gas chromatographic separation of the volatiles in the sample at block 104. Using the apparatus shown in FIG. 1, the eluent from the GC column is split between the mass spectroscopy detector and the cryotrap and olfactory port. The eluent going to mass spectroscopy is detected and analyzed at block 106 and preferably provides a chromatogram for analysis and segmentation. The eluent from the column going to the cryotrap is sequestered at block 108 for olfactory port characterization by a human assessor at block 110. This provides a base olfactory characterization for the whole composite of aroma compounds that are extracted from the sample at block 102.

The elution profile from the column detected at block 106 is evaluated and fractions are selected at block 108. Selected fractions of volatiles chosen by retention time on the column are collected and recombined within the cryotrap at block 108. Fractions from any part of the column elution profile can be combined for evaluation or excluded. In one embodiment, several cryotraps and olfactory ports are provided with the instrument so that different fractions of the eluent can be collected simultaneously from the same sample run through the column. In another embodiment, a run using the steps at block 102 through block 108 are repeated for each fraction or combination of fractions that are collected and the unwanted volatiles are directed to waste.

The collected fractions and combined fractions are then characterized at block 112 with olfactometry. In one embodiment, only those fractions and combinations of fractions that are collected are characterized by mass spectrometry and olfactometry.

The olfactory characterizations of the whole aroma as well as the fractions and combinations of fractions at block 110 and 112 preferably use a vocabulary of sensory descriptors that are compiled. In one embodiment, sensory profiles of the fractions and combinations of fractions are compiled and compared based on the vocabulary of sensory descriptors that is compiled. The contributions of each fraction and combinations of fractions to the overall aroma can then be determined. The phenomena of synergy, addition, inhibition and masking between different aroma compounds can also be evaluated.

Once the contribution of certain fractions to the overall aroma is identified, the concentrations of key fractions can be manipulated to evaluate the effect on the overall aroma. In one embodiment, multiple fractions are collected of the key fractions that are identified and combined with the whole sample and then evaluated.

Optionally, the compounds that are identified by mass spectrometry detection at block 106 can be related to the composition of the fractions and combinations of fractions and to the sensory profiles at block 112. The influences of the chemical structures of components on the appearance of masking or synergy or other phenomenon, sensory descriptors and on the whole aroma can be examined. In addition, it will be possible to characterize subsets of molecules and their aroma activity and to identify patterns and form predictive models.

The invention may be better understood with reference to the accompanying examples, which are intended for purposes of illustration only and should not be construed as in any sense limiting the scope of the present invention as defined in the claims appended hereto.

Example 1

In order to demonstrate the functionality of the apparatus and methods, an apparatus configured like the embodiment shown in FIG. 1 was constructed and tested. An Agilent model 6890 gas chromatograph/5972 mass selective detector (GC-MSD) was modified with the addition of a Dean's switch apparatus (Agilent Technologies, Santa Clara, Calif.), auxiliary pressure controller (EPC, Agilent), splitter (Gerstel), cryotrap (Micro Cryo-trap and model 971 controller, Scientific Instrument Services, Ringoes N.J.) and olfactometry port (ODP-2, Gerstel, Linthicum, Md.). Deactivated fused silica was used for all transfer lines. The transfer line from the Deans switch to the splitter was 4 m in length. The dimensions of the transfer line from the splitter to the MSD were 1 m×0.15 mm; the dimensions of the transfer line from the splitter to the olfactory port were 1 m×0.25 mm resulting in a 1.86:1 split ratio between the olfactory port and MSD.

Chromatographic separation was performed using a 30 m×25 mm i.d.×0.25 mm film thickness DB-5MS column (J&W, Folsom, Calif.). The inlet was maintained at 240° C. in splitless mode. Helium was used as the carrier gas and was held at constant pressure at 15.5 psi. Flow at the Deans switch was controlled with the auxiliary pressure controller and was maintained at 3.4 psi. The SPME assembly was introduced manually into the inlet and allowed to desorb for a total of 10 minutes. The oven was held at 60° C. for 3 minutes, then ramped up to 150° C. at a rate of 3° C./min, then ramped up to 325° C. at a rate of 30° C./min and held for 1 minute for a total runtime of 40 minutes. The olfactory port transfer line was maintained at 60° C. and the MSD transfer line was maintained at 260° C. After a 0.5 minute solvent delay, the mass spectrometer scanned from m/z 50-230. With the Deans switch 1 set in the "off" position, the flow was directed to the splitter, MSD, cold trap, and olfactory port. When set to the "on" position, the flow was directed to waste. The switch is programmed in the "runtime" tab of the Enhanced Chemstation Software (Hewlett Packard, version B.01.00) to direct the flow over the course of the runtime as desired by the operator.

The apparatus was tested by evaluating the aroma of lavender (*Lavandula angustifola* 'Hidcote Blue') flowers with a series of perceptual interaction and omission experiments (Table 1; FIG. 2). The volatile chemical composition of lavender, a potently aromatic herb with numerous culinary, cosmetic, and fragrance uses, has previously been characterized, but there are no lavender impact compounds that are currently identified. This suggests that "lavender" aroma character arises from the perception of a mixture of volatiles rather than a single molecule, making this an ideal mixture for evaluation of perceptual interactions using the gas chromatography recomposition-olfactometry GC-R) approach.

Lavender (*Lavandula angustifola* 'Hidcote Blue') flowers were collected from the garden of the Robert Mondavi Institute for Wine and Food Sciences at the University of California, Davis. Flowers (0.50 g) were weighed and placed in a 20 mL amber glass headspace vial and sealed with a crimp cap with a PTFE-faced silicone septum (Supelco, St. Louis, Mo.). A Solid Phase Microextraction fiber (2 cm length, 50/30 um divinylbenzene/carboxen/polydimethylsiloxane coating (DVB/CAR/PDMS), Supelco) was used for extraction. The fiber was exposed to the headspace of the vial for 30 minutes at room temperature, then withdrawn and immediately desorbed in the GC inlet.

Example 2

By programming the switches to either cryotrap or exclude peaks or peak regions, two types of evaluations can be performed. In perceptual interaction experiments, all of the chromatogram except for a small section of peaks is cut away, and the section of interest is assessed as a mixture. In omission experiments, small groups of peaks (or individual peaks) are cut away and the rest of the compounds in the chromatogram are smelled as a mixture at the olfactory port by trained panelists.

To demonstrate the olfactometry aspects of the invention, lavender volatiles were introduced to the gas chromatograph capillary column for separation. Based on retention time, the Deans Switch sent specific packets of volatiles to the cryotrap according to one of 10 programs (W, O1-O3, P1-P6; Table 1, FIG. 3). At the conclusion of each separation run, the cold trap was heated and the mixture was sniffed and described by a sensory panelist. The W condition, analogous to a full aroma reconstitute, contained all the volatiles of lavender, with conditions O1-O3 and P1-P6 omitting groups of these volatiles for descriptive comparison to the aroma of the W sample and to lavender flowers.

Three panelists (Females, ages 28-45 with previous sensory experience) smelled each of the ten mixtures in triplicate and generated terms to describe the perceived odor. Before smelling each mixture, each panelist first smelled and described a standard of lavender flowers, picked at the same time as the flowers used for SPME sampling, and also rated how well the sample mixture represented the aroma of the standard on a scale of 0-10.

For each of the ten mixtures, the panelist was first presented with a reference of lavender flowers (1 g) picked at the same time as the flowers used for sampling. Flowers were then sampled from a sealed vial using HS-SPME and the fiber injected into the GC-MS inlet for analysis. A trained panelist was directed to sniff deeply at the nose cone of the olfactory while the cold trap was rapidly heated, to describe the qualities of the odor mixture by listing its aroma attributes, and finally to rate how well the aroma represented the reference whole lavender flowers on a scale of 0-10. For each of the 10 mixtures (1 full chromatogram, 6 perceptual interaction and 3 omission mixtures), the frequency of the appearance of each descriptor was tabulated by mixture and a correspondence analysis was performed.

The procedure conditions and aroma descriptors for mixtures of volatiles from the lavender chromatograms are found in Table 1. For omission experiments, the Deans switch was programmed to remove specific time sections of the chromatogram, yielding three separate mixtures with sections from 0-16 minutes, 16-25 minutes, and 25-40 minutes cut out, respectively. The sections remaining for each mixture were trapped and released at the end of the run to be smelled and described by the panelist. Three panelists repeated each experiment in triplicate.

For Perceptual Interaction experiments, the Deans switch was programmed to isolate small sections of the chromatogram to be smelled as mixtures by cutting to waste the rest of the chromatogram. Each mixture was trapped and released at the end of the run to be smelled and described by the panelist. Three panelists repeated each experiment in triplicate.

The terms used to describe the 10 mixtures were tabulated by frequency of use. A correspondence analysis (CA) was performed on the contingency table of Mixtures (Rows)× Descriptors (Columns) with frequency of descriptor appearance per mixture as cell contents. A 3-way Analysis of Variance (ANOVA) with all 2-way interactions was performed with rated representativeness of each mixture compared to a fresh lavender standard as the response factor and panelist, mixture, and replicate as main effects. A Tukey's Honest Significant Difference multiple comparisons test (HSD) was performed on the representativeness ratings. The R statistical computing package was used for all statistical analyses.

Sensory panelists generated and used 82 terms; some terms which had overlapping meanings were combined into single descriptors. For example, any citrus-related descriptors (lemon, orange, citrusy, etc.) were combined into a single "citrus" descriptor; likewise "lavender" and "fresh lavender" were collapsed into "lavender"; "hay" and "dried hay" were combined into "haylike", and "smoky" and "burnt" were combined into "smoke". Descriptors used three or more times for a given mixture are found in Table 1.

"Fresh Lavender" and "Dried Lavender" were both predominant descriptors for the "Whole Volatile" recombination mixture W. Of the more chemically complex omission mixtures O1-O3, only O1, which incorporated the section of volatiles eluting from 16-40 minutes of the lavender chromatogram and omitted volatiles eluting between 0-16 minutes, was described as having "fresh lavender" properties. O1 overlapped with O2 from 25-40 minutes and with O3 from 16-25 minutes and incorporated the perceptual mixtures P3-P6, however, none of these other omission or perceptual mixtures had fresh or dried lavender among their commonly used descriptors.

This suggests that there are two subsets of compounds, the first eluting between 16-25 minutes and the other eluting between 25-40 minutes, that are each necessary for the perception of "lavender character" but are not alone sufficient for inducing this perception without some mixing with compounds in the other elution group. These results also suggest that "lavender character" is an emergent perceptual property arising from the mixing of these volatiles or some subset thereof.

Example 3

Figure 4:
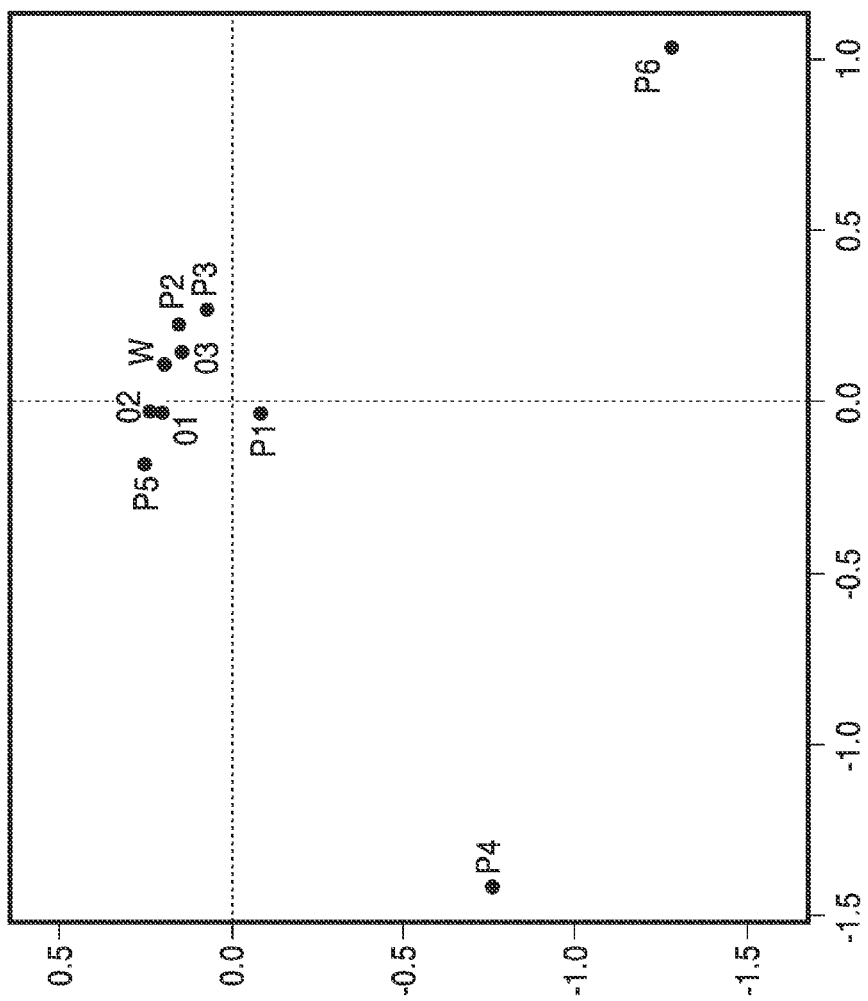
FIG. 4 is a graph depicting correspondence analysis of lavender volatile mixtures of the mixtures of Table 1.
Figure 5:
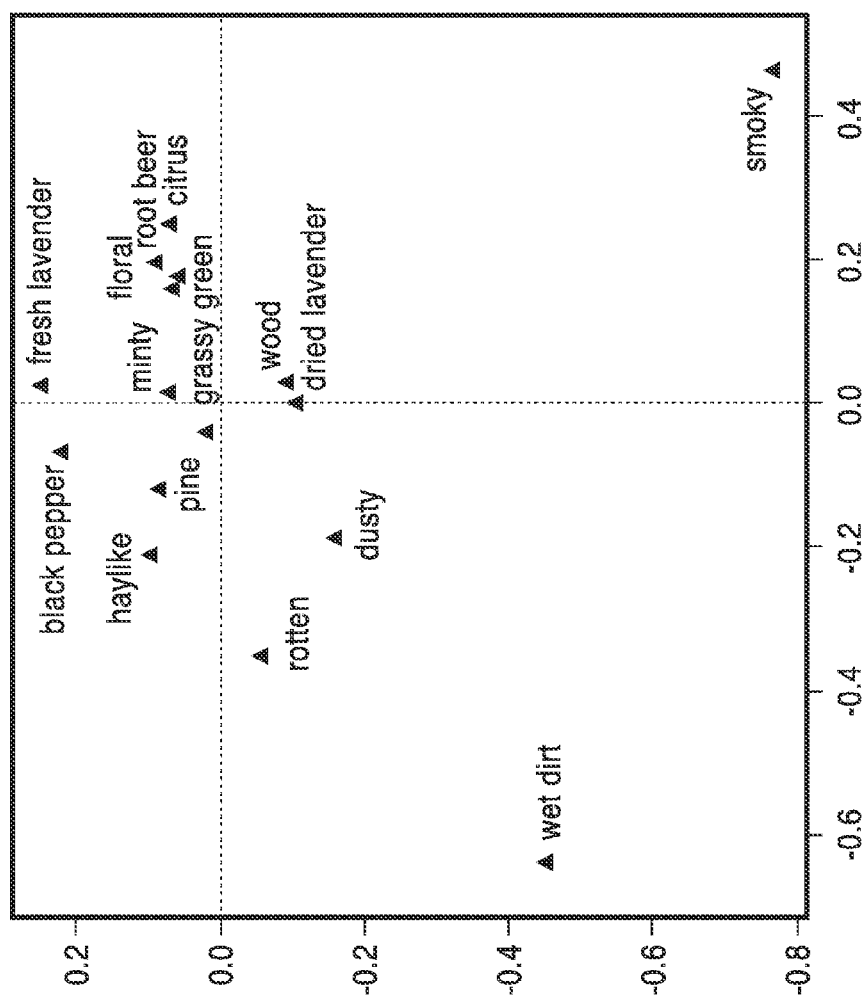
FIG. 5 is a graph depicting correspondence analysis of lavender volatile mixture descriptors of the mixtures of Table 1. Samples P1, P5, and P6 are significantly less representative of the aroma of flowering lavender than sample W, which incorporates all the volatiles in flowering lavender.

To further evaluate the separations, Correspondence Analysis was performed on the descriptors-by-mixtures data matrix to compare dimensionally-reduced latent trends in the sensory profiles of the mixtures to the differences evident in top descriptors for each mixture. Correspondence Analysis separates dissimilar categories in space; mixtures and sensory descriptors spaced closely together share more similarities than those spaced further apart. FIG. 4 is a graph of the volatile mixtures of lavender and FIG. 5 is a graph of lavender volatile mixture descriptors. The abbreviations for the mixtures in FIG. 4 correspond to those found in Table 1. Terms generated by the panelists to describe the perceived odor of from each Experimental Condition described in Table 1 were tabulated by frequency of use and used for the Correspondence Analysis.

As seen in the plot of FIG. 4, removing more volatiles generally results in greater dissimilarity between a given mixture and the all-volatiles-included mixture W. The relatively tight clustering of the all-volatiles-included (W) mixture and omission mixtures O1-O3 in the Correspondence Analysis reflects the sensory similarity of these mixtures. Perceptual mixtures P2 and P3 also cluster nearby, reflecting some of the overlapping characteristics of these mixtures.

The location of mixture W in the center of the main cluster in the Correspondence Analysis shown in FIG. 4, suggests its aroma is perceived, in part, as a sensory average of some of the less-complex mixtures. However, a truly averaged perceptual character would be in the center of the plot. The fact that mixture W is offset from the geometric center implies that the mixing-dependent interactive effects of the lavender volatiles perceived in mixture W play a noticeable role in affecting its overall aroma character. Mixture W shares many similar descriptors (Table 1) with O1-O3 and P2 and P3, but all of these except O1 lack a dominant lavender character.

Mixtures P1 and P5 are close to the central cluster of the plot of FIG. 4 but are approximately equi-distant in space from mixture W. This reflects some of the similarities in the descriptors that P1 and P5 share with mixture W, but also reflects the domination of the aromas of these mixtures by either a unique character ("black pepper") in the case of P5, or the relative simplicity of the aroma in the case of P1 (Table 1, FIG. 4). The comparative distancing of mixtures P4 and P6 from the other mixtures reflects the relative uniqueness of their aroma descriptors.

Locations of descriptors suggest that along the first (x) dimension of FIG. 5, there is a distinction between fresher, more "sweet" and flower-associated terms on the right side and earthier, heavier aroma terms on the left. Borrowing more qualitative terms from the tradition of perfumery (which at its essence is the craft of observing and optimizing the perceptual effects of mixing volatiles), a rough progression is observed from left to right along the x-axis, of base, middle, and top-note related terms.

Along the second (y) dimension, the separation ranges from more highly shared or composite aroma descriptors to more unique or unitary ones. The separation in the second (y) dimension is dominated by the marked difference of P4 and P6 from each other and from the rest of the mixtures, and correspondingly by their unique descriptors "wet dirt" and "smoky" in FIG. 5. Generally, the terms on the other arm of the y-dimension tend to be shared by multiple mixtures, or reflect more composite aroma characteristics.

While sample P1 appears to be the closest to the central or average sample in this set, it is clearly separated from the cluster centered around mixture W along the third (z) dimension. The third dimension also further separates mixture P5 from the central W-associated cluster and increases the distinction between "grassy/green"–"woody" descriptors on one side and "dried lavender"–"black pepper" descriptors on the other.

Importantly, the correspondence analysis, while unable to describe absolute differences, provides valuable information not only on the sources of variation in the complex sensory data but also on the interrelationships of the mixtures and their sensory properties.

In aroma psychophysics (i.e., the study of concentration-perception relationships for the human sensory system), additivity and interaction effects of stimuli are often studied. These psychophysical and perception studies often include human panelists and the evaluation of mixtures of odorants; the focus, however, tends to be on gathering data about the human panelists' sensory system.

In contrast, the present invention, although informed by the practices of sensory psychophysics, attempts to bring focus to sensory phenomena as related to perception of an everyday smell object, in this case lavender. The sensory data describe examples of additive and synergistic effects of aroma quality. For example, as sub-sets of lavender volatile mixtures approach the chemical complexity of the whole sample, there is an increasing cross-utilization or addition of descriptors from other similar mixtures and ultimately, the appearance of complex sensory terms that are only evident at certain levels of chemical complexity. Comparing some of the simpler mixtures to the rest of the sensory data, there are also instances of qualitative masking effects—aromas which dominate simpler mixtures, such as black pepper for P5, smoky for P6, and wet dirt for P4 are less evident or dominant when present in more complex mixtures.

Example 4

The method used to create an extract of volatile compounds can alter the aroma of the extract and failure to obtain a representative sample can lead to unreliable conclusions about the composition of the aroma active components. While many extraction methods have been employed in order to produce an aroma extract, the creation of a representative aroma can be very difficult for complex matrices, and the sensory representativeness of this extract is not evaluated in all cases. Here, the aroma of the SPME extracts of lavender corresponded closely to the original product after a 25 minute extraction at room temperature (Table 1). However, the SPME fiber coatings do exhibit some analyte selectivity and may not always be able to produce an appropriate extract. Importantly, the GC-R approach described herein provides a quick, easy, and effective tool to assess the representativeness of an extract regardless of the extraction method employed.

Since the SPME extraction produced an aroma mixture representative of lavender, it was possible to perform omission and interaction experiments based on a starting point nearly identical to the intact lavender sample, eliminating "reconstitution discrepancy." Selected mixtures of compounds were omitted to assess the resulting aroma. Cut times were chosen to include chemically similar compounds in the same mixture, for example, monoterpene acetate esters in mixture P5 and sesquiterpenes in mixture P6. However, the omitted compounds/fractions in a theoretical GC-R procedure need not be contiguous. It is possible, for example, to remove every other chromatographic peak, to remove only the 3rd and 17th peak, etc. while trapping and evaluating the remaining components. The apparatus could additionally be used to perform single omission experiments, where compounds are omitted one at a time to screen for potential impact odorants, or perceptual interaction experiments where only 2 or 3 peaks are included in the mixture.

The flexibility in the compounds that can be removed and assessed is only limited by the rapid switching time of the Deans switch. By using a Mass Spectrometric detector, compounds in the sample can be identified. In the present case, volatiles were identified by matching their mass spectra to the NIST 05 Mass Spectral Library (National Institute of Standards and Technology, Gaithersberg, Md.) and to chemical standards. However, an obvious advantage of performing an omission experiment in this manner is that the compounds need not be identifiable or available to perform the experiment. Reconstitution experiments often require the experimenter to perform lengthy and labor-intensive syntheses to prepare a component for the reconstitution model only to find that the component can be omitted with no change in the overall aroma of the solution. Furthermore, there is always some fraction of the total compounds identified that are not included in the reconstitution because they are deemed to have a concentration too low to have an effect on the overall aroma. However, compounds with low odor activity values often still have a considerable effect on the overall aroma of the mixture.

While compounds with low OAVs may be important to the overall aroma of the mixtures, the opposite case can also occur, and the sensitivity of the human nose is frequently orders of magnitude greater than an instrumental detector. As a result, the nose may detect an aroma where there is no peak on a chromatogram. Particularly as compared to reconstitution studies, this is another distinct advantage of the GC-R approach since even compounds not detected by the detector (MS, FID) will be included in the aroma sample as it is assessed by a subject at the olfactometry port.

Traditionally, full separation of volatile compounds on the chromatographic column is necessary in order to meaningfully describe the aroma character of the eluent by GC-R since it simplifies the recognition task for the assessor. However, it is more often the case that a complex mixture of aroma compounds is responsible for the overall aroma of a food or beverage. In addition, a mixture of two or more odorants can frequently lead to an aroma that is not similar to any of its individual components. Using a GC-R technique, any of these interactions can readily be investigated; and all that is necessary to characterize any type of aroma interaction is a sample of the food, beverage, flower, etc. of interest. Compounds detectable by GC-O but not GC-MS, compounds below putative aroma thresholds, compounds at levels that cannot be quantified, and compounds not commercially available or easily synthesized can all be perceptually analyzed if they are found in one or more aromatic samples available to the researcher.

Figure 6:
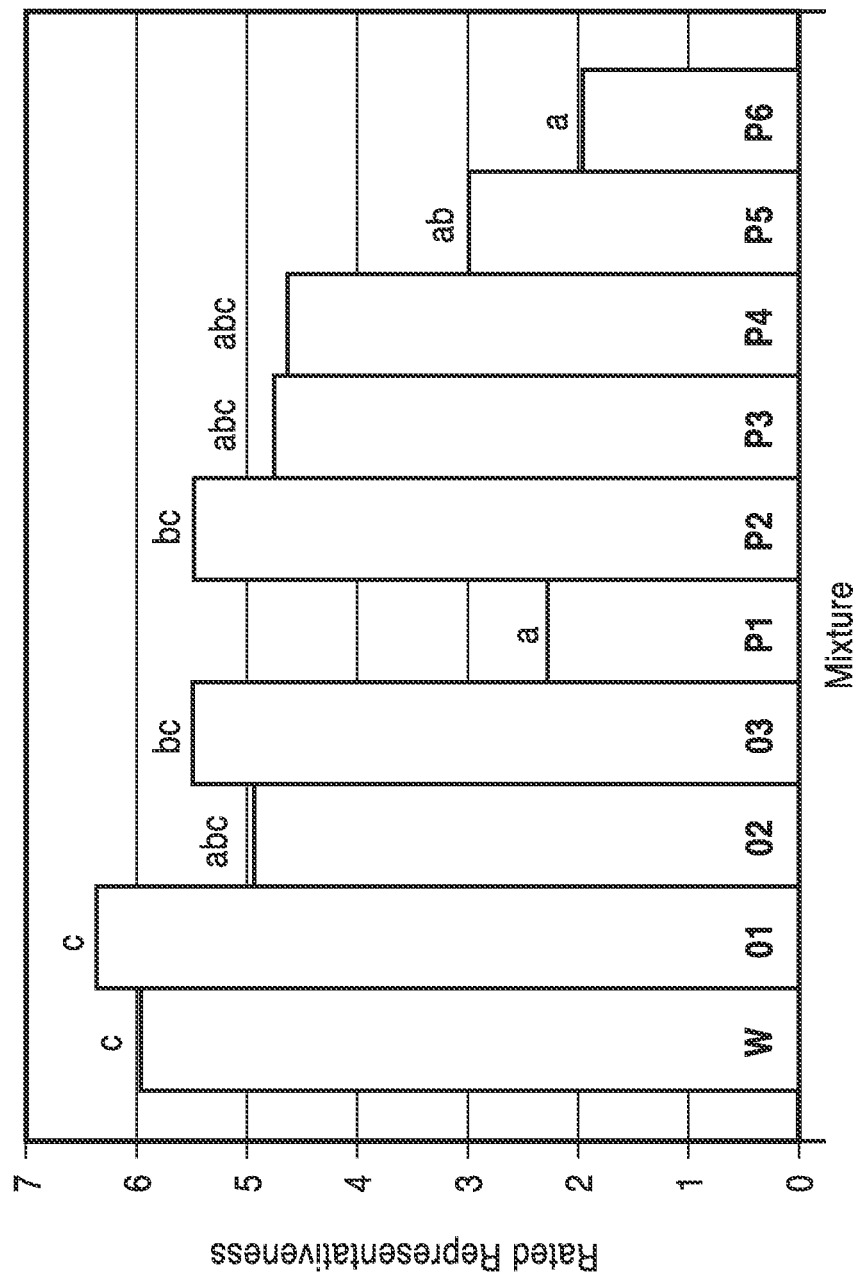
FIG. 6 is a graph of the rated representativeness of the aroma samples of Table 1 of lavender volatile compound mixtures created in-instrument.

The rated representativeness of the aroma of samples W, O1-O3, and P1-P6 as compared by panelists to the aroma of whole flowering lavender is shown in FIG. 6. Letters a, b, c refer to the mixture's Significant Difference from each other—if two samples do not share a letter, they are significantly different. Comparing the aroma of the GC-R mixtures in this study to the aroma of whole lavender flowers, panelists found that mixtures P1, P5, and P6 were significantly less representative of the aroma of the whole flowers than mixtures W, O1-O3 and P2-P4 as seen in FIG. 5. These samples also tended to have either fewer commonly used descriptors or descriptors not found for other mixtures such as "black pepper" for P5 and "smoke" for P6.

The sensitivity of the human nose can be orders of magnitude higher than an instrumental detector. As a result, the nose may detect an aroma where there is no peak on a chromatogram. This provides a distinct advantage of the GC-R approach we describe, particularly as compared to reconstitution studies, since by this method, even compounds not detected by the detector (MS, FID) will be included in the aroma sample as it is assessed at the olfactometry port. Furthermore, our GC-R approach does not require that the identified compounds be available in pure form to the researcher, as would be required in a reconstitution experiment.

Traditionally, full resolution of analytes on the chromatographic column is necessary in order to meaningfully describe the aroma character of the eluent by GC-O since it simplifies the recognition task for the assessor. However, it is more often the case that a complex mixture of aroma compounds is responsible for the overall aroma of a food or beverage. In addition, it has been shown that a mixture of two or more odorants can frequently lead to an aroma that is not similar to any of its components. With this GC-O device, two compounds can be arbitrarily mixed together to determine the resulting aroma. Compounds with low odor activity values are often disregarded in flavor characterization but have been shown to have a considerable impact on the overall aroma of a mixture. Using this apparatus, these interactions can be investigated. In fact, one or both of the compounds being mixed need not be identified or available on hand to assess the aroma of the interaction. Furthermore, they do not even need to be detectable using the instrumental detector. If there exists a detectable aroma peak by GC-R that is not detectable by GC-MS/FID, these compounds can still be retained and mixed together.

From the discussion above it will be appreciated that the invention can be embodied in various ways, including the following:

1. A method for characterization and analysis of aroma mixtures, comprising: (a) extracting volatiles from a sample to form a mixture of volatiles; (b) separating components of the mixture of volatiles with a gas chromatographic column; (c) detecting eluents from the gas chromatographic column with a detector; (d) dividing eluents from the gas chromatographic column into fractions; (e) combining fractions of eluents from the gas chromatographic column; (f) selecting fractions and combinations of fractions for characterization; and (g) characterizing selected fractions and combined fractions with olfactometry.

2. A method as recited in any of the previous embodiments, further comprising: creating an elution profile of detected eluents; segmenting the profile to designate eluent fractions; and using the profile as a map to designate combinations of eluent fractions.

3. A method as recited in any of the previous embodiments, wherein the eluent from the gas chromatographic column is divided equally over time to designate the fractions.

4. A method as recited in any of the previous embodiments, further comprising: identifying component compounds within the selected fractions and combinations of fractions.

5. A method as recited in any of the previous embodiments, further comprising: compiling a sensory profile of identified component compounds and olfactometry data for each selected fraction and combined fractions.

6. A method as recited in any of the previous embodiments, wherein the detector comprises a mass spectrometer.

7. A method as recited in any of the previous embodiments, further comprising: assembling sensory descriptors from olfactometry; and performing correspondence analysis on the descriptors to evaluate sensory similarity between fractions.

8. A method for characterization and analysis of aroma mixtures, comprising: (a) extracting volatiles from a sample to form a mixture of volatiles; (b) separating components of the mixture of volatiles with a gas chromatographic column; (c) detecting eluents from the gas chromatographic column with a detector; (d) characterizing the eluents with olfactometry; (e) profiling detected eluents; (f) segmenting the profile of detected eluents; (g) dividing eluents from the gas chromatographic column into fractions; (h) combining fractions of eluents from the gas chromatographic column; (i) selecting fractions and combinations of fractions for characterization; and (j) characterizing selected fractions and combined fractions with olfactometry.

9. A method as recited in any of the previous embodiments, wherein the characterization with olfactometry further comprises: assembling sensory descriptors from scent assessors; and performing correspondence analysis on the descriptors to evaluate sensory similarity between fractions, combinations of fractions and a whole aroma.

10. A method as recited in any of the previous embodiments, wherein the elution profile is segmented by equal time increments.

11. A method as recited in any of the previous embodiments, wherein the elution profile is segmented by detected volatile components and groups of volatile components.

12. A method as recited in any of the previous embodiments, further comprising: characterizing all fractions with olfactometry; and comparing characterized fractions and combinations of fractions with characterizations of the whole sample aroma.

13. A method as recited in any of the previous embodiments, further comprising: identifying compounds contained in fractions and combinations of fractions selected for characterization.

14. A method as recited in any of the previous embodiments, further comprising: collecting fractions from multiple separation runs of volatiles through the a gas chromatographic column; combining one or more collected fractions with extracted volatiles; characterizing combined volatiles with olfactometry; and comparing characterized combined volatiles with characterizations of the whole sample aroma.

15. A method as recited in any of the previous embodiments, wherein the collected fractions are the same fraction in the elution profile.

16. A method as recited in any of the previous embodiments, wherein the detector comprises a mass spectrometer.

17. A method for characterization and analysis of aroma mixtures, comprising: (a) extracting volatiles from a sample to form a mixture of volatiles; (b) separating components of the mixture of volatiles with a gas chromatographic column; (c) detecting eluents from the gas chromatographic column with a detector; (d) profiling eluents from the gas chromatographic column detected with the detector; (e) dividing eluents from the gas chromatographic column into fractions; (f) trapping the eluent fractions in a plurality of traps; (g) characterizing the trapped eluent fractions with olfactometry; (h) combining fractions of eluents from the gas chromatographic column; (i) characterizing the combined eluent fractions with olfactometry; (j) comparing characterized fractions and combinations of fractions with characterizations of the whole sample aroma and detected elution profile.

18. A method as recited in any of the previous embodiments, further comprising: identifying compounds contained in fractions and combinations of fractions.

19. A method as recited in any of the previous embodiments, further comprising: trapping fractions from multiple separation runs of volatiles through the a gas chromatographic column; combining one or more trapped fractions with extracted volatiles; characterizing combined volatiles with olfactometry; and comparing characterized combined volatiles with characterizations of the whole sample aroma.

20. A method as recited in any of the previous embodiments, further comprising: mixing one or more trapped fractions with another trapped fraction; combining one or more mixed fraction with extracted volatiles; characterizing combined mixed fractions and volatiles with olfactometry; and comparing characterized combined volatiles with characterizations of the whole sample aroma.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

Experimental GC-R Conditions And Aroma Descriptors For Mixtures Of Volatiles From The Lavender Chromatograms

| Experimental Condition | Abbreviation | Chromatogram Sections Included in Mixture | Top Descriptors |
|---|---|---|---|
| Whole Chromatogram | W | 0-40 minutes | Floral, citrus, dried lavender, fresh lavender, mint, wood |
| Omission 1 | O1 | 16-40 minutes | Citrus, fresh lavender, dusty, floral, grassy/green, mint, pine, rotten |
| Omission 2 | O2 | 0-16 + 25-40 minutes | Citrus, hay-like, floral, pine, root beer |
| Omission 3 | O3 | 0-25 minutes | Citrus, grassy/green, mint, wood, soapy |
| Perceptual Interaction 1 | P1 | 0-11 minutes | grassy/green, wood |
| Perceptual Interaction 2 | P2 | 11-16 minutes | Floral, wood |
| Perceptual Interaction 3 | P3 | 16-20.5 minutes | Citrus, floral, soapy |
| Perceptual Interaction 4 | P4 | 20.5-25 minutes | Dusty, rotten, wet dirt |
| Perceptual Interaction 5 | P5 | 25-32 minutes | Black pepper, hay-like, citrus, floral, grassy/green |
| Perceptual Interaction 6 | P6 | 32-40 minutes | Citrus, smoke |
| Lavender Flowers Reference | Reference | Not separated; whole lavender flowers | Citrus, floral, fresh lavender, mint, wood, hay, dried lavender, grassy/green |

We claim:

1. A method for characterization and analysis of aroma mixtures, comprising:
   (a) extracting volatiles from a sample to form a mixture of volatiles;
   (b) separating components of said mixture of volatiles with a gas chromatographic column;
   (c) detecting eluents from said gas chromatographic column with a detector;
   (d) dividing said detected eluents from said gas chromatographic column into fractions;
   (e) combining said fractions of eluents from said gas chromatographic column;
   (f) selecting said fractions and combinations of said fractions for characterization; and
   (g) characterizing said selected fractions and said selected combinations of fractions with olfactometry.

2. A method as recited in claim 1, further comprising:
   creating an elution profile of detected eluents;
   segmenting the profile to designate eluent fractions; and
   using said profile as a map to designate combinations of eluent fractions.

3. A method as recited in claim 1, wherein said eluents from said gas chromatographic column are divided equally over time to designate the fractions.

4. A method as recited in claim 1, further comprising:
   identifying component compounds within said selected fractions and combinations of fractions.

5. A method as recited in claim 1, further comprising:
   compiling a sensory profile of identified component compounds and olfactometry data for each selected fraction and combined fractions.

6. A method as recited in claim 1, wherein said detector comprises a mass spectrometer.

7. A method as recited in claim 1, further comprising:
   assembling sensory descriptors from olfactometry; and
   performing correspondence analysis on the descriptors to evaluate sensory similarity between fractions.

8. A method for characterization and analysis of aroma mixtures, comprising:
   (a) extracting volatiles from a sample to form a mixture of volatiles;
   (b) separating components of said mixture of volatiles with a gas chromatographic column;
   (c) detecting eluents from said gas chromatographic column with a detector;
   (d) characterizing said eluents with olfactometry;
   (e) profiling detected eluents;
   (f) segmenting the profile of detected eluents;
   (g) dividing said detected eluents from said gas chromatographic column into fractions;
   (h) combining said fractions of eluents from said gas chromatographic column;
   (i) selecting said fractions and said combinations of fractions for characterization; and
   (j) characterizing said selected fractions and said selected combinations of fractions with olfactometry.

9. A method as recited in claim 8, wherein said characterization with olfactometry further comprises:
   assembling sensory descriptors from scent assessors; and
   performing correspondence analysis on the descriptors to evaluate sensory similarity between said selected fractions, said selected combinations of fractions and a whole aroma.

10. A method as recited in claim 8, wherein said elution profile is segmented by equal time increments.

11. A method as recited in claim 8, wherein said elution profile is segmented by detected volatile components and groups of volatile components.

12. A method as recited in claim 8, further comprising:
    characterizing all fractions with olfactometry; and
    comparing characterized fractions and combinations of fractions with characterizations of the whole sample aroma.

13. A method as recited in claim 8, further comprising:
identifying compounds contained in fractions and combinations of fractions selected for characterization.

14. A method as recited in claim 8, further comprising:
collecting fractions from multiple separation runs of volatiles through the gas chromatographic column;
combining one or more collected fractions with extracted volatiles;
characterizing combined volatiles with olfactometry; and
comparing characterized combined volatiles with characterizations of the whole sample aroma.

15. A method as recited in claim 14, wherein said collected fractions are the same fraction in the elution profile.

16. A method as recited in claim 8, wherein said detector comprises a mass spectrometer.

17. A method for characterization and analysis of aroma mixtures, comprising:
   (a) extracting volatiles from a sample to form a mixture of volatiles;
   (b) separating components of said mixture of volatiles with a gas chromatographic column;
   (c) detecting eluents from said gas chromatographic column with a detector;
   (d) profiling eluents from said gas chromatographic column detected with the detector;
   (e) dividing said detected eluents from said gas chromatographic column into fractions;
   (f) trapping said eluent fractions in a plurality of traps;
   (g) characterizing said trapped eluent fractions with olfactometry;
   (h) combining said fractions of eluents from said gas chromatographic column;
   (i) characterizing said combined eluent fractions with olfactometry;
   (j) comparing said characterized fractions and said characterized combinations of fractions with characterizations of the whole sample aroma and detected elution profile.

18. A method as recited claim 17, further comprising:
identifying compounds contained in said fractions and said combinations of fractions.

19. A method as recited in claim 17, further comprising:
trapping fractions from multiple separation runs of volatiles through the gas chromatographic column;
combining one or more trapped fractions with extracted volatiles;
characterizing said combined volatiles with olfactometry; and
comparing characterized combined volatiles with characterizations of the whole sample aroma.

20. A method as recited in claim 19, further comprising:
mixing one or more trapped fractions with another trapped fraction;
combining one or more mixed fraction with extracted volatiles;
characterizing combined mixed fractions and volatiles with olfactometry; and
comparing characterized combined volatiles with characterizations of the whole sample aroma.

\* \* \* \* \*